| United States Patent [19] | [11] Patent Number: 4,634,664 |
| Oestberg | [45] Date of Patent: Jan. 6, 1987 |

[54] PROCESS FOR THE PRODUCTION OF HUMAN MONO-CLONAL ANTIBODIES

[75] Inventor: Lars Oestberg, Vienna, Austria

[73] Assignee: Sandoz Ltd., Basel, Switzerland

[21] Appl. No.: 459,731

[22] Filed: Jan. 20, 1983

[30] Foreign Application Priority Data

Jan. 22, 1982 [CH] Switzerland ............................ 409/82

[51] Int. Cl.$^4$ ...................... C12P 21/00; C12N 15/00; C12N 5/00; C12R 1/91
[52] U.S. Cl. .................................. 435/68; 435/172.2; 435/240; 435/241; 935/93; 935/96; 935/106; 935/100; 530/387
[58] Field of Search .............. 435/68, 240, 241, 172.2, 435/948; 935/93, 96, 100, 106

[56] References Cited

U.S. PATENT DOCUMENTS

| 4,195,125 | 3/1980 | Wacker | 935/96 |
| 4,377,513 | 3/1983 | Sugimoto et al. | 435/68 |
| 4,383,034 | 5/1983 | Sugimoto | 435/68 |
| 4,383,035 | 5/1983 | Sugimoto | 435/68 |
| 4,383,036 | 5/1983 | Sugimoto | 435/68 |
| 4,472,500 | 9/1984 | Milstein et al. | 435/948 |
| 4,529,694 | 7/1985 | Lazarus et al. | 435/172.2 |

FOREIGN PATENT DOCUMENTS

| 0044722 | 1/1982 | European Pat. Off. | 435/948 |
| 0068763 | 1/1983 | European Pat. Off. | |
| 2079313 | 1/1982 | United Kingdom | 935/96 |

OTHER PUBLICATIONS

Foung et al., J. Immunol. Methods, 70, 83 (1984).
Teng et al., Proc. Natl. Acad. Sci. USA, 80, 7308 (1983).
Williams et al., Cell, 12, 663, (1977).
Bron et al., Proc. Natl. Acad. Sci, USA, 81, 3214 (1984).
Oestberg et al., Hybridoma, 2, 4, 361 (1983).
Croce et al., Eur. J. Immunol., 10, 486 (1980).
Tucker et al., Hybridoma, 3, 2, 171 (1984).
Dorland's Illustrated Medical Dictionary, 24th ed., 1715, 26th ed., 1477.
Nowinski et al, "Human Monoclonal Antibody Against Forssman Antigen", Science 210, pp. 537–539 (1980).
Shulman et al, "A Better Cell Line for Making Hybridomas Secreting Specific Antibodies", Nature 276, pp. 269–270 (1978).
Fazekas et al, "Production of Monoclonal Antibodies: Strategy and Tactics", Journal of Immunological Methods 35, pp. 1–21 (1980).
Davidson et al, "Genetics of Cultured Mammalian Cells, as Studied by Somatic Cell Hybridization", National Cancer Institute Monograph #48, pp. 21–30 (1976).
Levy et al, "Rescue of Immunoglobin Secretion from Human Neoplastic Lymphoid Cells by Somatic Cell Hybridization", Proceedings of the National Academy of Sciences 75(5), pp. 2411–2415 (1978).

*Primary Examiner*—Charles F. Warren
*Assistant Examiner*—John Edward Tarcza
*Attorney, Agent, or Firm*—Gerald D. Sharkin; Robert S. Honor

[57] ABSTRACT

Hybridoma cell line made by fusing a xenogeneic hybridoma cell to a genetically compatible substance producing cell. Such hybridomas can be used i.a. for the production of antibodies.

21 Claims, No Drawings

PROCESS FOR THE PRODUCTION OF HUMAN MONO-CLONAL ANTIBODIES

The present invention is concerned with hybridoma cell lines and methods for producing them, as well as their use for producing particular substances for example antibodies.

Hybridoma is the term applied to cells formed by fusion of an "immortalizing" cell (in particular a myeloma cell) to a "normal" non-transformed cell usually chosen for its ability to produce a particular substance (e.g. a lymphocyte cell to produce antibodies) to form a hybrid. These hybrids can be selected and cloned to obtain cell lines producing substances having a single structure and/or property. In particular such hybridomas formed with lymphocytes can be used to produce monoclonal antibodies.

The development of hybridoma technology in recent years has been directed to obtaining cell lines which are both stable and have a high and specific production of a particular substance which it is desired to obtain. There have been various approaches to this problem which because of their historical origin have been largely concentrated in the field of immunoglobulins/antibodies.

A study of previous activities in this field provides a overview of the types of problem encountered and the various solutions so far attempted.

The original impulse for research into hybrid cell lines producing monoclonal products came from the field of immunobiology the products being monoclonal antibodies. Conventional anti-sera usually contain a very large number of antibodies which differ structurally in the antigen binding site but each bind to the same antigen with a greater or lesser degree of avidity and/or specificity. In addition conventional anti-sera also contain a large number of antibodies directed against other antigens and reflecting previous defensive reactions of the host individual from whom the antiserum was obtained. Whilst for most purposes such "broad" antisera were sufficient it was felt that provision of more specificity and reproducibility would mark a significant advance and provide a scientific tool of tremendous potential, particularly in the field of diagnosis and therapy.

The first and now classical solution was that described by Köhler and Milstein [*Nature*, 256, 495-497 (1975)] who succeeded in fusing pre-immunized mouse spleen cells to "drug" sensitive mouse myeloma cells. The thus immortalised fused cells could be grown in vitro and cloned from the single cell level to produce a homogenous cell population producing a homogenous antibody population (monoclonal antibodies). By selection between the many unique cells and selective recloning it was possible to obtain and grow cells which produce antibodies of the desired antigen specificity.

Mouse antibodies produced in this fashion have proved useful for research and diagnostic purposes and some have even been used therapeutically in humans. It would however involve a considerable advance in human immunoglobulin therapy if human antibodies of similar specificity and reproducibility could be obtained in this way. This would also reduce the danger of sensibilisation. Several approaches to the problem of producing such human antibodies in vitro have been tried but have so-far been largely unsuccessful. These include:

(i) Transformation of normal human lymphocytes with Epstein-Barr virus (EBV). This method has met with little success as cells of this type require a long and tedious process to become established and are extremely difficult to clone and select.

(ii) Fusion of normal (human) lymphocytes with human myeloma cells. This method represents an obvious analogy to the mouse-mouse hybridoma approach but faces the problem that in the human-system only one myeloma cell line has been made broadly available and this was found to be contaminated with mycoplasma which impedes successful fusions.

(iii) Fusion of normal human lymphocytes to an EBV-transformed human lymphoblastoid B-cell line. Whilst this is probably the most reliable and reproducible method yet described it suffers from the basic in vitro drawback encountered with lymphoblastoid cells: they are extremely difficult to clone and, as they represent an early stage in B-cell differentiation lineage, their capacity to produce and secrete antibodies is about 10 times lower than that of true myelomas.

(iv) Fusion of human lymphocytes to mouse myeloma. This method produces cells with the same excellent in vitro characteristics as the mouse-mouse hybridomas but with the great disadvantage that such hybrids have an inherent genetic instability. One particularly troublesome result of this is that they expel the human chromosome on which the genome for forming the kappa light chain of the immunoglobulin is located.

In summary therefore procedure (i) is too tedious and inefficient to be practicable; procedure (ii) is not yet of any practical significance; procedure (iii) is the best of those currently available; and procedure (iv) whilst viable cannot maintain productivity even with extremely fastidious cloning procedures.

Whilst both the above discussion and most work done to date has been concentrated on antibody production it is clear that the "productive" cell partner can be selected for secretion of a particular substance which it is desired to obtain and fused to the "immortalising" cell line.

We have now found that by using a xenogeneic hybridoma cell as parent for further fusion to another cell it is possible to obtain a hybridoma of greatly improved stability.

The invention therefore concerns:

A hybridoma cell line comprising an immortalizing cell fused to a cell producing a predetermined substance characterized in that the immortalizing cell is a xenogeneic hybridoma cell and in that the substance producing cell is genetically compatible with the non-transformed partner in the xenogeneic hybridoma.

The stability of such cells lies in their ability, if correctly cultured, to maintain production of a predetermined substance such as an antibody.

In a particular aspect the xenogeneic hybridoma chosen as immortalizing cell is a myeloma hybrid which has lost its own ability to produce immunoglobulin. An example of such a xenogeneic hybridoma cell would be that between a myeloma cell and a lymphocyte cell. Examples of suitable myeloma cells are those obtained from mice and rats and will preferably produce no immunoglobulin. These myelomas can themselves be hybrids (e.g. mouse myeloma/mouse lymphocyte) which are in effect myelomas. Such a cell is e.g. the mouse SP-2 myeloma cell line. This is then fused to e.g.

a lymphocyte obtained from another species e.g. a human lymphocyte cell.

In a preferred embodiment xenogeneic hybridomas resulting from such fusions which no longer produce immunoglobulin are chosen for further fusing to substance producing cells.

These xenogeneic hybridomas present a more benign environment for further stability in terms of chromosome loss.

The xenogeneic hybridomas used for immortalization are made drug resistant prior to further fusing in conventional manner. A particular method is selection for 8-azaguanine resistance.

The hybridomas thus obtained provide stable parents for further fusing. The other fusion partner is selected for its ability to produce a predetermined substance—an example would be choice of a lymphocyte to produce an antibody—and is genetically compatible with the non-transformed partner in the xenogeneic hybridoma.

In order to obtain the required degree of specificity it is desirable to pre-sensitize the chosen cell to produce the desired substance. This can for example be achieved for the case of antibodies by immunization of a host with a particular antigen and subsequent collection of immunocytes (i.e. cells which are immunologically competent) which produce corresponding antibodies.

These can for example be spleen, lymphnode or blood cells.

The fusion of the xenogeneic hybridoma cell parent to the substance producing cell takes place in conventional manner. This usually involves incubating comparable amounts of each cell in a suitable medium together with a substance which promote fusion (e.g. PEG 1500). Selection of the desired hybrids is again conventional and can be carried out in selective media (e.g. HAT [hypoxanthine/aminopterin/thymidine] if the immortalizing cells does not contain the hypoxanthine phosphoribosyl transferase).

The resulting cell lines are stable and produce high yields of antibody.

They can also be cloned and reselected if required or desired.

The invention therefore also concerns a method of producing a stable hybridoma cell line which comprises making a xenogeneic hybridoma cell parent drug-resistant fusing this to a substance producing cell which is genetically compatible with the non-myeloma partner in the xenogeneic hybridoma and selecting a desired hybrid.

Antibody production using these cells can be carried out along conventional lines either in vitro in suitable media (e.g. these containing diluted fetal calf serum) or in vivo by injection into a host (nude or athymic mouse or rat) and harvesting of the ascitic fluid. Depending on the method chosen one or more purification steps may be required.

The invention also concerns the production of antibodies employing such cell lines.

Whilst it is clear that simple hybridoma cell lines with the desired properties will, for economical reasons, be preferred it will also be possible if desired or required to fuse such cell lines further.

A typical antibody producing hybridoma according to the invention would be one formed from a mouse myeloma fused with a human lymphocyte as parent and then fusion with a pre-sensitised human lymphocyte as antibody producer. Any of the myeloma cells can, if appropriate, themselves be hybrids (as e.g. in the SP-2 mouse line which is itself a mouse/mouse hybrid).

Examples of literature describing conventional techniques and previous work are
1. Köhler, G. and Milstein, C. Nature, 256, 495–497 (1975)
2. Nadler, L. M. et al., Cancer Research, 40, 3147–3154 (1980)
3. Cosimi, A. B. et al., N. Engl. J. Med., 305, 308–314 (1981)
4. Zurawski, V. R. et al., Science, 199, 1439–1441 (1978)
5. Koskimies, S., Scand. J. Immunol., 11, 73–77 (1980)
6. Steinitz, M. et al., Nature, 287, 443–445 (1980)
7. Olsson, L. and Kaplan, H. S., Proc. Natl. Acad. Sci. U.S.A., 77, 5429–5431 (1980)
8. Croce, C. M. et al., Nature, 288, 488–489 (1980)
9. Nowinski, R. et al., Science, 210, 537–539 (1980)
10. Croce, C. M. et al., Proc. Natl. Acad. Sci. U.S.A., 76, 3416–3419 (1979)
11. Galfre, G. et al., Nature 266, 550, 1977
12. Miller, R. A. et al., N. Engl. J. Med. 306, 517, 1982
13. Sikora K., et al., Lancet, i 11, 1982 and e.g. U.S. Pat. No. 4.172,124 EP Appln. Pub. Nos. 0043 718 and 0044 722 and the recently published book on monoclonal antibodies by McIntyre.

The present invention by employing a xenogeneic fusion parent (which has lost its ability to produce predetermined substances) enables hybridomas to be obtained which are stable, fast growing, easily clonable and have a high production rate of the desired substance, e.g. human antibodies.

Human antibodies produced according to the invention can be employed as conventional for such antibodies. Examples of such fields of use are:

Infectious diseases: Viruses (cytomegalo, varicella zoster, herpes simplex, hepatitis A & B, rubella etc.). Bacteria (anti-toxins, anti-cell wall). Fungi (candida).

Malignant diseases: Antibodies against all kinds of malignant tumors, with and without conjugation to toxins.

Intoxication: Anti-poison antibodies (antidotes, digitalis, opiates, tricyclic anti-depressants, barbiturates etc.).

Anti-idiotypes: Anti-anti pancreatic $\beta$-cell, anti-anti acetylcholin receptor, anti-rheumatoid factor.

Blood-group antigens: Anti-Rh

Transplantation: Anti T-cell to curb rejections, enhancing antibodies to reduce the stimulating capacity of the graft.

Allergy: IgG antibodies to allergens, alternative to hyposensitization.

Hormones: Chorionic gonadotropin antibodies for use as contraceptives.

The hybridoma cells themselves can also be used as a source for nRNA if cloning of immunoglobulin genes is attempted.

In a particular embodiment according to the present invention the SP-2 cell line, which was originally itself a hybridoma between P3-X63-Ag8 line and mouse spleen cells which produce antibodies to sheep red blood cells is used which has lost its ability to produce antibodies (C. F. M. Shulmann et al., Nature 276, 269, 1978).

It is obtainable e.g. from the NIGMS Human Genetic Mutant Cell Repository Ref. GM 35669 A (see US DHHS 1982 Catalog of Cell Lines).

This cell line is made drug resistant and then fused with normal human peripheral lymphocytes by conventional techniques [C.F. G. Galfre et al., Nature 266, 550 (1977) and R. Nowinski et al., Science 210/537 (1980)].

A large number of hybrids is obtained and after approximately 5 weeks 5 clones are selected which show fast growth and no antibody production. These cells are selected for resistance to 8-azaguanine and with three of these lines it is possible to obtain mutants which are resistant to 20 μg/ml of 8-azaguanine. These cells are at the same time sensitive to Hypoxantine-Aminopterin-Thymidine (HAT) medium which showed that they had lost their ability to produce hypoxanthine phosphoribosyl transferase.

One of these lines (SPAZ4) is then fused in vitro with human tonsillar lymphocytes employing $10^8$ tonsillar cells with $2 \times 10^7$ SPAZ4 cells. The fusion is carried out according to standard procedures. For comparative purposes the SP/2 cell line is also fused. The resulting cell populations are selected in HAT-medium in order to recover the required hybrids. As soon as all cells in unfused control cultures are killed, the HAT medium is replaced by normal non-selective growth medium.

After two weeks of growth the initial test for antibody production is performed and it is found that all 47 cultures from each of the fusions were producing human antibody. On re-testing after a further 4 weeks however it is discovered that 83% of the SPAZ-4 hybridomas are still producing antibody compared with 55% of the SP/2 hybridomas. A high production rate is found in 28% of the SPAZ-4 lines compared with only 3% of the SP/2's.

In view of the fact that a major factor in loss of antibody production is the loss of L-chain genome a specific test for light chain production is performed. It is found that 67% of the SPAZ-4 lines produce kappa chains and 88% lambda. The corresponding values for SP/2 are 39% und 61% respectively (These percentages of course comparable for the particular experiment and immunoglobulin (Ig) employed). Results are summarised in table I. It will be noted that SPAZ-4 is in all cases superior to SP/2 especially as regards the values for "strong" production which are the most important ones from a practical point of view. All these experiments are performed with uncloned cells in order to maximise pressure against the stable clones (stable clones carry more genetic material and always grow less well than cells which have succeeded in expelling their "unnecessary" chormosomes).

Experiments have however been made to clone the cells. Results so far obtained indicate that not one single, stable and productive SP/2 hybrid is obtained (i.e. no line where all growing cells produced antibody). In SPAZ-4-hybrids on the other hand it is possible to derive such clones.

The present invention makes it possible to obtain substantially better results than previously known methods by solving the problem of instability whereby it is worth mentioning that even the "classical" mouse-mouse hybridomas are instable and fastidious subcloning is always necessary they are however practicable to work with. The degree of instability shown with SPAZ-4 hybridomas is lower than for mouse-mouse hybridomas and that it is thus even more practicable to work with them.

The following examples illustrate the invention.

EXAMPLE 1

Production of the SPAZ-4 line

Peripheral blood lymphocytes (PBLs) are isolated from heparinised blood of a healthy donor by centrifugation on Ficoll-Isopaque. After washing, $10^8$ PBLs are mixed with $5 \times 10^7$ SP/2 cells in 50 ml of Dulbeccos H21 medium adjusted to pH 8.0. The cells are pelleted together at $600 \times g$ for 5 minutes after which the supernatant is carefully removed. Keeping the cells at 37° 1 ml of 50% PEG 4000 in H21 is slowly added during 1 minute. A further 10 ml of H21 is added during 2 minutes. The cells are collected by centrifugation (pelletting) and resuspended in 55 ml of HAT medium (HAT medium: Dulbeccos H21 with 20% fetal calf serum, 10% NCTC 109, 1% Non-essential aminoacids, 0.5% pyruvate 0.2 U/ml insulin, 1 mM oxalacetic acid, $10^{-4}$M hypoxanthine, $4 \times 10^{-7}$M aminopterin and $1.6 \times 10^{-3}$M thymidine.) and seeded into 528.0 ml cultures in flat-bottomed tissue-culture microplates. Fresh HAT-medium is given to the cultures every 3–5 days for two weeks after which the medium is changed to HT-medium (Dulbeccos H21 with 10% FCS, $10^{-4}$ hypoxanthine and $1.6 \times 10^{-3}$ thymidine). After the 15th day samples are taken to test for human antibody. Five cultures are selected showing good growth and zero antibody production. These are then selected for production of 8-azaguanine resistant sublines.

The five cell-lines are seeded at $2 \times 10^5$ cells/ml in Dulbeccos H21 with 10% FCS and 20 μg/ml of 8-azaguanine. From 3 of these cultures it is possible after a couple of weeks to recover viable, growing cells. One of these is the SPAZ-4 which is sensitive to HAT and is employed for further testing.

EXAMPLE 2

Fusion with tonsillar lymphocytes

Tonsills from a child are trimmed of connective tissue and passed through a fine mesh metal net to give a single-cell preparation. In order to reduce the number of red cells all cells are fractionated on Ficoll-Isopaque. Of the resulting cell population $10^8$ cells are fused to $2 \times 10^7$ either SPAZ-4 or SP/2 cells with a procedure identical to that described in Example 1. The cells are later seeded into 47 0.5 ml cultures in HAT-medium which this time is supplemented with 0.5 μg/ml of cyclosporin A. After one day 0.5 ml of HAT-medium without cyclosporin A is added. Already on the third day 50% of the medium is changed to HT-medium. After this the cells are maintained in HT-medium with passage every 3–5 days.

Testing for immunoglobulin production

A traditional ELISA (Enzyme-linked Immunosorbend Assay) system is used. Rabbit anti-human immunoglobulin is attached to Nunc EIA plates at a dilution of 1:400 in a pH 9.6 bicarbonate buffer. After washing the plates the culture supernatants are incubated for 30' at 37°. After once more washing, the incubations are treated with peroxidase-conjugated rabbit anti-human IgG, IgM, IgA reagent (Miles-Yeda) at 1:400 dilution. After washing the enzyme-reaction is developed with 1,2-phenylendiamine-dihydrochloride and $H_2O_2$.

The test for light-chain production is made in exactly the same way except that goat anti-human lambda or goat anti-human kappa reagent (Tago) at 1:3000 dilution is used instead of rabbit anti-human IgG, IgM, IgA.

The results are evaluated on a Titertek Multiscan Elisa-photometer and the values "4" and "7" in table 1 refer to low and high readings respectively from this photometer.

EXAMPLE 3

Production of mono-clonal antibodies against influenza Typ A and B (after in vivo immunisation)

The influenza vaccine employed is SANDOVAC® containing hemaglutinin and neuraminidase from A/-Bangkok, A/Brazil and B/Singapore. Three healthy volunteers are immunized and bled on days 3, 7, 10, 14 and 17. Each time 50–60 ml of blood is drawn from the cubital vein into heparin containing syringes. The lymphocytes are isolated by centrifugation on Ficoll-Paque (Pharmacia) and washed twice in saline before use.

The fusion parents are
(a) SPAZ-4 (cf Ex. 1)
(b) SP/2 (see above)
(c) GM 1500 human lymphoblastoid cell made 8-azaguanine resistant at WISTAR INSTITUTE (produces human IgG2 kappa)

The SPAZ-4 and SP-2 are fused identically. The myeloma ($10^7$ cells) and the human lymphocytes (approx. $3 \times 10^7$ cells) are mixed in a test tube in the presence of DMEM serumfree medium at pH 8.0. The cells are centrifuged together at $600 \times g$ for 5 min. The resulting pellet is treated with 50% PEG 4000 for 1 min. after which the PEG is slowly diluted with medium. After one wash the cells are seeded into 176 100 μl cultures in DMEM-HAT medium containing 20% fetal calf serum. The cells are cultured at 37° C. in a humid 10% $CO_2$-atmosphere.

The GM 1500 cells ($10^7$ cells) are mixed with the human lymphocytes (approx. $3 \times 10^7$ cells) in serumfree DMEM pH 8.0, and centrifuged at $600 \times g$ for 5 min. The pellet is treated with 50% PEG 6000 for 5 min. during which the cells are centrifuged at $600 \times g$. After this time the PEG is slowly diluted with medium. After one wash the cells are seeded into 176 100 μl cultures in RPMI 1640-HAT medium containing 20% fetal calf serum. The cells are cultured at 37° C. in a humid 5% $CO_2$-atmosphere.

A total of 35 fusions (15 to GM 1500, 14 to SPAZ-4 and 6 to SP-2) involving 6160 cultures (2640 with GM 1500, 2464 with SPAZ-4 and 1056 with SP-2) are made.

The media are changed in the cultures when ever cell proliferation makes it necessary, as a rule every 3–5 days. Presence of anti-influenza antibodies in the supernatants is assayed with an ELISA method: the relevant influenza antigens are catched into micro plate wells (Nunc), the supernatant added and allowed to interact with the antigen. After washing a peroxidase-conjugated rabbit anti-human IgG, IgA, IgM (Miles) is added to the wells. After incubation the unbound peroxidase-conjugate is washed away and color-substrate for the enzyme added to the wells. The reaction is estimated visually and documented with a Titertek microplate photometer. Cultures showing positive results are cloned at limiting dilution conditions in 88 new wells seeding the cells at 1 cell/culture in 100 μl of DMEM+20% fetal calf serum together with mouse thymocyte feeder cells (SPAZ-4 and SP-2 derived cells) or in RPMI 1640+20% fetal calf slerum on MRC-5 feeder cells (GM 1500 derived cells). Productive cells are grown up in larger scale and frozen in liquid $N_2$.

A total of 86 cultures (58 from GM 1500, 26 from SPAZ-4, 2 from SP-2) were cloned. Quite liberal criteria are applied in deciding if a cell should be cloned or not which accounts to the low yield of truly positive cells after cloning. This has to be done as GM 1500 for example produces no high production cells. From the SPAZ-4 cells four positive clones are identified from the SP-2 one which however, was not a hybrid but rather a spontaneously arising EB-virus transformed cell. No producing cell is derived from GM 1500.

The results of the fusion are summaried in the table.

| Day | GM 1500 Cultures fused | GM 1500 Cultures pos. | SPAZ-4 Cultures fused | SPAZ-4 Cultures pos. | SP-2 Cultures fused | SP-2 Cultures pos. |
| --- | --- | --- | --- | --- | --- | --- |
| 3 | 528 | 0 | 528 | 0 | 176 | 0 |
| 7 | 528 | 0 | 352 | 2 | 176 | 0 |
| 10 | 528 | 0 | 528 | 1 | 176 | 0 |
| 14 | 528 | 0 | 528 | 0 | 354 | 1§ |
| 17 | 528 | 0 | 528 | 1 | 176 | 0 |
| Sum | 2640 | 0 | 2464 | 4 | 1056 | 1 |

§Spontaneous EBV-cell.

The five positive cell-lines are recloned several times and grown on a larger scale. This results in the demise of the EBV-line (it is well known that such cell colonies do not survive low density cloning).

The 4 positive SPAZ-4 hybridoma cell lines were identified as C15, C28, C29 and C75.

EXAMPLE 4

Production of anti-influenza hybridoma (after in vitro immunization)

Human spleen cells are seeded at $10^6$/ml in 2 ml aliquots in Falcon 2051 tubes; a total of $34 \times 10^6$ cells are used. An optimal amount of sucrose density gradient purified A/Bangkok virus is added and the cultures are maintained in RPMI 1640 medium with 5% human heat-inactivated plasma for 101 hours at 37° C. in an atmosphere of 5% $CO_2$ in air. The recovered $9 \times 10^6$ cells are fused to a similar number of SPAZ-4 cells as described in Example 3. The cells are seeded into 176 cultures and grown in Dulbecco's MEM containing 20% fetal calf serum, HAT and 1 μg/ml cyclosporin A. After 2 days the HAT medium is gradually displaced by HT medium and thereafter changed at intervals of 4–5 days. The cultures are screened for anti-influenza antibodies on days 12 and 19 after fusion and the positive cultures are cloned. A positive clone (identified as B2) is obtained which is capable of large scale growth and use for in vitro preparation of "chemical" amounts of pure antibody.

EXAMPLE 5

Characterization of human anti-influenza monoclonal antibodies (a) Antibody/C15

The antibody is of the IgG 1 class and has a kappa light chain. The antibody reacts to all tested viruses of the influenza A type (H1N1, H2N2, H3N2), it is most probably directed against the nucleoprotein of the virus. The antibody has no neutralizing activity in vitro and no protective effect in vivo.

(b) Antibody/C28

The antibody is of the IgG 1 class and has a lambda light chain. The antibody reacts only to influenza virus of the H3N2 type, it is most probably directed against the hemagglutinin of the virus. The antibody has a strong neutralizing effect in vitro and a dramatic protective activity in vivo. It can neutralize all H3N2 viruses tested, i.e. the viruses from 1968, 1969, 1973, 1974, 1975, 1977, 1979, and 1980.

When tested with the 1973 A/Port Chalmers on MDCK cells an antibody preparation containing 1.5 mg/ml of pure antibody is found to have a neutralizing titer of 12 800. In the same experiment a preparation of standard human immunoglobulin (Sandoglobulin) at a concentration of 60 mg/ml is found to have a neutralizing titer of 50. This means that the monoclonal antibody C28 on a protein equivalent level has a potency which is 10 240 times higher than normal immumoglobulin. It is pertinent in this context to point out that anti-influenza antibody is one of the pre-dominant components in a normal immunoglobulin preparation which means that antibodies with the same neutralizing potency as C28 but directed against e.g. cytomegalo virus or varicella-zoster virus, where the level of antibody in normal immunoglobulin preparations is fairly low, the relative potency might reach much higher values.

(c) Antibody/C29

The antibody is of the IgG 1 class and has a lambda light chain. The antibody reacts to influenza type B/Singapore, it has not been tested against any other type B virus. It has no activity against type A virus.

(d) Antibody/C75

The antibody is of the IgG 3 class and has a kappa light chain. The antibody reacts only to viruses of the H3N2 type, it is most probably directed against the hemagglutinin of the virus. It has no neutralizing activity in vitro and no protective effect in vivo.

(e) Antibody/B2

The antibody is of the IgG 1 class and has a kappa light chain. It reacts only to viruses of the H3N2 type, and is most probably directed against the hemagglutinin of the virus. The antibody has no neutralizing effect in vitro, it has not been tested for in vivo protection.

TABLE 1

| cell | day | immunoglobulin % 4 | 7 | kappa % 4 | 7 | lambda % 4 | 7 |
|---|---|---|---|---|---|---|---|
| SPAZ-4 | 4 | 83 | 28 | | | | |
| SP/2 | 4 | 55 | 3 | | | | |
| SPAZ-4 | 5 | | | 67 | 25 | 88 | 46 |
| SP/2 | 5 | | | 39 | 13 | 61 | 17 |
| SPAZ-4 | 6 | 36 | 9 | | | | |
| SP/2 | 6 | 25 | 2 | | | | |

I claim:

1. A hybridoma cell line comprising an immortalizing cell fused to a cell producing a predetermined human antibody, the immortalizing cell comprising a xenogeneic hybridoma cell fused from an immortalizing cell and a non-transformed partner cell, said human antibody producing cell being genetically compatible with said non-transformed partner cell.

2. A hybridoma cell line as claimed in claim 1 wherein the antibody producing cell is of the same species as the non-transformed partner in the xenogeneic hybridoma cell parent.

3. A hybridoma cell line as claimed in claim 2 wherein the antibody producing cell partner and the non-transformed partner in the xenogeneic hybridoma cell parent are of human origin.

4. A hybridoma cell line as claimed in claim 3 wherein the antibody producing cell is presensitized either in vitro or in vivo to produce the predetermined antibody.

5. A hybridoma cell line as claimed in claim 2 wherein the antibody producing cell is a lymphocyte.

6. A hybridoma cell line as claimed in claim 5 wherein the lymphocyte is of human origin.

7. A hybridoma cell line as claimed in claim 5 wherein the lymphocyte has been pre-sensitized either in vivo or in vitro to produce antibodies.

8. A hybridoma cell line as claimed in claim 7 wherein the myeloma partner in the xenogeneic hybridoma cell is a rodent myeloma which does not produce immunoglobulin.

9. A hybridoma cell line as claimed in claim 8 wherein the rodent myeloma is a mouse myeloma.

10. A hybridoma cell line as claimed in claim 9 wherein the mouse myeloma is provide by the SP-2 cell line.

11. A hybridoma cell line as claimed in claim 1 wherein the xenogeneic hybridoma cell parent has lost its ability or is otherwise unable to produce a predetermined substance.

12. A hybridoma cell line according to claim 11, wherein the hybridoma is a stable (mouse×human)-×human hybridoma cell line capable of producing human antibodies of a predetermined specificity.

13. A hybridoma cell line as claimed in claim 1 which comprises a xenogeneic hybridoma cell formed by fusion of a mouse myeloma cell with a human lymphocyte as parent cell and a pre-sensitized antibody producing human-lymphocyte as substance producing cell.

14. A method of producing the hybridoma cell line of claim 1 which comprises making a xenogeneic hybridoma cell drug resistant, and fusing this cell to an antibody producing cell which is genetically compatible with the non-transformed partner in the xenogeneic hybridoma and selecting a desired hybrid.

15. A method as claimed in claim 14 wherein the fusion partners employed are chosen from those as described in claim 3.

16. A method as claimed in claim 14 wherein selection of a desired hybrid takes place on the basis of lack of sensitivity to HAT and assay for the ability to produce the predetermined substance.

17. A method as claimed in claim 14 wherein the xenogeneic hybridoma has lost its ability or is otherwise unable to produce a predetermined substance.

18. A process for the production of a predetermined antibody which comprises culturing a hybridoma cell line as claimed in claim 1 in an in vitro or in vivo culture medium therefor and thereafter isolating the antibody from said medium.

19. A method as claimed in claim 18 wherein in vivo culturing takes place in a athymic (nude) mouse or rat.

20. A (mouse×human)×human hybridoma cell line capable of producing human antibodies of a predetermined specificity wherein both human cells are not transformed.

21. A stable (mouse×human)×human hybridoma cell line capable of producing human antibodies of a predetermined specificity wherein each human cell is non-transformed.

* * * * *